(12) United States Patent
Tu et al.

(10) Patent No.: US 6,807,444 B2
(45) Date of Patent: Oct. 19, 2004

(54) APPARATUS AND METHODS FOR MONITORING TISSUE IMPEDANCE

(76) Inventors: Hosheng Tu, 15 Riez, Newport Coast, CA (US) 92657; Rodolfo C. Quijano, 27451 Lost Trail Dr., Laguna Hills, CA (US) 92653

( * ) Notice: Subject to any disclaimer, the term of this patent is extended or adjusted under 35 U.S.C. 154(b) by 361 days.

(21) Appl. No.: 10/050,307

(22) Filed: Jan. 16, 2002

(65) Prior Publication Data

US 2003/0088189 A1 May 8, 2003

Related U.S. Application Data

(63) Continuation-in-part of application No. 10/011,062, filed on Nov. 5, 2001.

(51) Int. Cl.[7] ................................................ A61B 5/00
(52) U.S. Cl. ...................................... 600/547; 600/549
(58) Field of Search .................................. 600/547, 549

(56) References Cited

U.S. PATENT DOCUMENTS

| | | | |
|---|---|---|---|
| 4,458,694 A | 7/1984 | Sollish et al. | |
| 4,860,744 A | 8/1989 | Johnson et al. | |
| 5,348,554 A | 9/1994 | Imran et al. | |
| 5,522,815 A | 6/1996 | Durgin, Jr. et al. | |
| 5,529,067 A | 6/1996 | Larsen et al. | |
| 5,755,663 A | 5/1998 | Larsen et al. | |
| 5,810,742 A | 9/1998 | Pearlman | |
| 5,967,976 A | 10/1999 | Larsen et al. | |
| 6,015,407 A | 1/2000 | Rieb et al. | |
| 6,055,452 A | 4/2000 | Pearlman | |
| 6,106,521 A | 8/2000 | Blewett et al. | |
| 6,109,270 A | 8/2000 | Mah et al. | |
| 6,176,857 B1 * | 1/2001 | Ashley | 606/32 |
| 6,212,433 B1 | 4/2001 | Behl | |
| 6,238,393 B1 | 5/2001 | Mulier et al. | |
| 6,241,666 B1 | 6/2001 | Pomeranz et al. | |
| 6,241,725 B1 | 6/2001 | Cosman | |
| 6,298,726 B1 | 10/2001 | Adachi et al. | |
| 6,308,097 B1 | 10/2001 | Pearlman | |
| 6,719,755 B2 * | 4/2004 | Sliwa et al. | 606/41 |
| 6,741,895 B1 * | 5/2004 | Gafni et al. | 607/138 |
| 2001/0001314 A1 * | 5/2001 | Davison et al. | 606/41 |
| 2002/0026127 A1 * | 2/2002 | Balbierz et al. | 600/567 |

FOREIGN PATENT DOCUMENTS

WO       WO 01/67098         9/2001

OTHER PUBLICATIONS

William Leventon, "New Imaging Techniques Detect Diminutive Danger Signs" MD&DI, p. 48–57, Oct. 2000.

* cited by examiner

*Primary Examiner*—Mary Beth Jones
*Assistant Examiner*—Matthew J Kremer

(57) ABSTRACT

A method and apparatus for differentiating in a given area of tissue a tumorous tissue from a normal tissue, the method comprising measuring a plurality of tissue impedance over a range of tissue temperatures and comparing the measured tissue impedance with reference tissue impedance of the normal tissue adapted for tissue differentiation. The management of tissue temperatures may be accomplished with a probe arrangement comprising two elements of different electromotive potential conductively connected at a probe junction, and passing an electrical current through the elements to reduce or raise a temperature of the probe junction in accordance with the Peltier effect.

20 Claims, 8 Drawing Sheets

APPARATUS AND METHODS FOR MONITORING TISSUE IMPEDANCE

RELATIONSHIP TO COPENDING APPLICATION

This patent application is a continuation-in-part application of application Ser. No. 10/011,062 filed Nov. 5, 2001, the entire contents of which are incorporated herein by reference.

FIELD OF THE INVENTION

The present invention relates generally to a medical apparatus for diagnosing tissue and methods of use, and more particularly, to a medical apparatus and methods for identifying abnormal tissue employing tissue impedance data over a range of tissue temperatures effected according to the Peltier effect for tissue diagnosis.

BACKGROUND OF THE INVENTION

Cancer and tumor are abnormal tissue that exhibits tissue characteristics different from those of the normal tissue. Among all cancer cases, breast cancer is historically the leading cause of death in women. The outlook for a wonder drug or vaccine to mitigate or cure the disease at any stage is not promising. It is known that our present methods of surgery, radiotherapy, and chemotherapy are effective for long-term survival if applied when the disease is detected early and confined locally to the lesion site.

According to a report from the National Cancer Institute (NCI), breast cancer is the most common form of cancer among women, excluding non-melanoma skin cancers. About one in eight women in the United States will develop breast cancer during her lifetime. About 192,200 women will learn they have invasive breast cancer in 2002, while 40,200 women will die from the disease. More than 85 million American women ages 20 and over are candidates for breast cancer screening. American Cancer Society and the National Comprehensive Cancer Network currently recommend annual mammograms for women identified as normal risk beginning at age 40 and for women identified as high-risk beginning at age 25.

The latest imaging techniques may detect diminutive danger signs and help recognize disease indicators during their early stage when treatment may be most beneficial. One established technique is mammography, which is used for early detection of small, treatable breast cancers. But mammography is not infallible. According to one estimate, mammography misses 10 to 15% of all malignancies. In cases where the test results are inconclusive, patients must usually undergo biopsy procedures, which can be uncomfortable and painful to patients.

This disclosure relates to a medical apparatus and methods of differentiating in a given area of tissue a tumorous tissue from a normal tissue by measuring tissue characteristics in situ across a range of tissue temperatures and comparing the measured tissue characteristics with those from reference normal healthy tissue adapted for tissue differentiation, wherein the tissue characteristics may comprise electric impedance signals, a derivative of impedance versus tissue temperature data, acoustic impedance signals and others.

It is known to measure the electrical impedance of tissue to determine aspects of tissue structure. A technique is available as "electrical impedance tomography" in which a number of impedance readings are taken at spaced apart locations on a region of the human body and an image derived from the data. Further, Brown et al. in PCT WO 01/67098 discloses a method of differentiating tissue types using impedance measurements over a range of frequencies. It has been shown that the tissue impedance decreases at higher frequencies, probably due to current penetration at the cell membrane.

Sollish et al. in U.S. Pat. No. 4,458,694, the disclosures of which are incorporated herein by reference, discloses a system in which the impedance between a point on the surface of the skin and some reference point on the body of a patient is determined. The reference prior art describes the use of a multi-element probe for the detection of cancer, especially breast cancer, utilizing detected variations of impedance in the breast. However, the skin surface impedance measurement is not site-specific for breast cancer diagnosis.

Pearlman in U.S. Pat. No. 5,810,742, No. 6,055,452, No. 6,308,097 and "New Imaging Techniques Detect Diminutive Danger Signs" by W. Leventon (MD&DI pp 48–57, October 2000), the disclosures of which are incorporated herein by reference, describe transspectral impedance scanning (T-scan) systems as a new mammography for cancer identification. The T-scan measures the movement of electricity through tissue because cancers have impedance values that are much lower than those of noncancerous tissue. It is further disclosed that the capacitance and conductance of malignant tissue are about 50 times greater than that of either normal tissue or benign lesions. However, the T-scan neither measures the site-specific minute tumor or cancer in vivo, nor manipulates the tested tissue at a range of temperatures suitable for enhancedly differentiating the impedance signal of the cancers from that of noncancerous tissue over a range of tissue temperatures.

The sonography uses high frequency sound waves to perform a wide variety of diagnostic examinations. The ultrasound frequencies typically range from about 20 kHz to above 300 MHz. The principles of diagnostic sonography rest in the tissue attenuation, reflectivity, transmission or scattering, which has been described elsewhere (C J Pavlin and F S Foster, Ultrasound Biomicroscopy of the Eye, Chapter 1, by Springer-Verlag 1995). The outer layer of an ultrasound transducer may be used as an element for impedance measurement.

Adachi et al. in U.S. Pat. No. 6,298,726, the entire contents of which are incorporated herein by reference, discloses an acoustic impedance measuring apparatus that emits ultrasonic waves to a target object and measures the acoustic impedance of the target object by ultrasonic waves fed back. The reference fails to teach manipulating the target tissue object at a range of temperatures to enhancedly differentiate the acoustic impedance signal of the cancer tissue object from that of noncancerous tissue object.

It would overcome the afore-mentioned disadvantages by providing an apparatus, such as a needle probe and a method of differentiating in a given area of tissue a tumorous tissue from a normal tissue, the method comprising measuring tissue impedance, electrically, acoustically or thermally, across a range of tissue temperatures and comparing the measured tissue impedance and/or the first impedance-temperature derivative at a tissue temperature of interest with reference counterparts of the normal tissue at same tissue temperature of interest adapted for enhanced tissue differentiation.

To maintain the tissue temperature over a range, say from 20° C. to 45° C., thermal energy and cryogenic cooling is provided selectively. Conventionally thermal energy could be clinically applied to the tissue by radiofrequency heating, while the cryogenic cooling could be provided by a circulating cooled medium in the probe. A radiofrequency probe with a liquid-cooled electrode is conventionally used to manipulate the tissue temperature over a range of clinical interest. However, such an apparatus is bulky and also cumbersome to handle the liquid cooling system. In one embodiment, the range of tissue temperatures of the present invention is about 20° C. to 45° C. that is suitable and physiologically compatible with the body tissue.

U.S. Pat. No. 5,348,554 to Imran et al. discloses a catheter system with a cooled electrode. Specifically, an electrode having a chamber therein is provided with a circulated cooling liquid to cool the electrode. U.S. Pat. No. 6,241,666 to Pomeranz et al., and U.S. Pat. No. 6,015,407 to Rieb et al. also disclose a catheter system with a modified cooled electrode, mostly with a liquid coolant arrangement that is bulky, expensive or poses unnecessary risk to a patient. The entire contents of the above-cited patents are incorporated herein by reference.

A radiofrequency catheter with a liquid-cooled electrode includes extra auxiliary equipments, such as a circulating pump, a cooling liquid source, control instruments, and accessories. As disclosed in U.S. Pat. No. 5,348,554, the cooled liquid is intended to cool the inner chamber of the tip electrode. However, the temperature of the outer surface of the electrode may rise to an unacceptable level resulting in tissue degradation, blood clot, or coagulation. As is well known to an ordinary technician skilled in the art that the resistive heat of radiofrequency ablation comes from the tissue-electrode contact surface. Even with a liquid-cooled setup thereof, the electrode temperature might be far above the cell necrosis temperature.

A probe for quantifying the impedance over a range of physiologically compatible tissue temperatures would be ideal for breast cancer diagnosis. Johnson et al. in U.S. Pat. No. 4,860,744 discloses a thermoelectrically controlled heat medical catheter, which is incorporated herein by reference. More particularly, Johnson et al. discloses a system and methods for providing controlled heating or cooling of a small region of body tissue to effectuate the removal of tumors and deposits, such as atheromatous plaque. Though Johnson et al. teaches a medical catheter in accordance with the Peltier effect adapted for thermoelectric heating/cooling for destruction of diseased tissue and/or tumors in various parts of the body, Johnson et al. does not disclose a method for manipulating the tissue temperatures so as to enhancedly differentiate the impedance signal of the cancers from that of noncancerous tissue over a range of tissue temperatures for tissue differentiation.

Larsen et al. in U.S. Pat. No. 5,529,067, No. 5,755,663, and No. 5,967,976 disclose methods and apparatus for use in procedures related to the electrophysiology of the heart, such as identifying or evaluating the electrical activity of the heart, diagnosing and/or treating conditions associated with the electrophysiology of the heart, entire contents of which are incorporated herein by reference. Specifically, Larsen et al. teaches an apparatus having thermocouple elements of different electromotive potential conductively connected at a junction and reducing the temperature of the junction in accordance with the Peltier effect for cooling the contacted heart tissue. However, Larsen et al. does not teach a method for diagnosing a target tissue comprising providing thermal or cryogenic energy to the target tissue and simultaneously or subsequently measuring tissue impedance over a range of tissue temperatures for tissue differentiation.

It is one object of the present invention to provide an apparatus for differentiating a tumorous breast tissue from a normal tissue, wherein the apparatus comprises electrode means for continuous or time-discrete measurement of tissue impedance over a range of tissue temperatures; instrument means for effecting and monitoring the tissue temperatures; and comparing the measured tissue impedance over at least a portion of the range of tissue temperatures with reference tissue impedance of the normal tissue adapted for tissue differentiation, wherein the reference tissue impedance is measured over the same range of tissue temperatures. There is a clinical need to screen the patients by a less invasive needle probe technique that is fast and reliable so as to lower the number of unnecessary biopsies performed each year.

SUMMARY OF THE INVENTION

In general, it is an object of the present invention to provide an apparatus and a method for diagnosing and/or treating a target tissue using a medical apparatus that is suitable for the intended applications in treating tumorous tissue, comprising a catheter, a probe, a needle probe, a cannula, an endoscopic instrument, a lapascopic instrument or the like.

It is another object of the present invention to provide an apparatus and a method of differentiating in a given area of tissue a tumorous tissue from a normal tissue, the apparatus comprising electrode means for measuring a plurality of tissue impedance over a range of tissue temperatures, instrument means for effecting and monitoring the tissue temperatures; and comparing the measured tissue impedance over at least a portion of the range of tissue temperatures with reference tissue impedance of the normal tissue adapted for tissue differentiation, wherein the reference tissue impedance is measured over the range of physiologically compatible tissue temperatures.

It is still another object of the present invention to provide an apparatus and a method of differentiating a tumorous tissue from a non-tumorous tissue by comparing the first impedance-temperature derivative at a tissue temperature of interest with reference first impedance-temperature derivative of the non-tumorous tissue at the tissue temperature of interest adapted for tissue differentiation.

In one embodiment, the method of affecting the tissue temperatures over the range of interest may be provided by a probe junction, the probe junction being conductively connected to two elements of different electromotive potential and electrical current being passed through the elements to reduce/raise temperature of the probe junction in accordance with the Peltier effect. The probe junction may be located adjacent or close to the electrode means for affecting the tissue temperature while measuring tissue impedance.

In another embodiment, the target tissue may be selected from a group consisting of tumor, cancerous tissue, arrhythmia, pulmonary vein, benign prostate hyperplasia, breast tumor, breast cancer, inflammation, atherosclerosis, vulnerable plaque, or the like. The therapeutic thermal energy may be selected from a group consisting of radiofrequency energy, microwave energy, laser energy, infrared energy, ultrasound energy, cryogenic energy, and combination thereof.

It is another object of the present invention to provide an electric impedance, acoustic impedance, or biochemical impedance over a range of tissue temperatures for tissue differentiation.

It is still another object of the present invention to provide an apparatus or a probe for treating tissue subsequent to identifying a tumorous tissue. The treatment methods may comprise thermal ablation, cryogenic ablation, delivering therapeutic means for treating the tumorous tissue at about the given area of tissue, wherein the therapeutic means is selected from a group consisting of drug, chemotherapy, radiation, and combination thereof.

BRIEF DESCRIPTION OF THE DRAWINGS

Additional objects and features of the present invention will become more apparent and the invention itself will be best understood from the following Detailed Description of Exemplary Embodiments, when read with reference to the accompanying drawings.

DETAILED DESCRIPTION OF EXEMPLARY EMBODIMENTS

Figure 1:
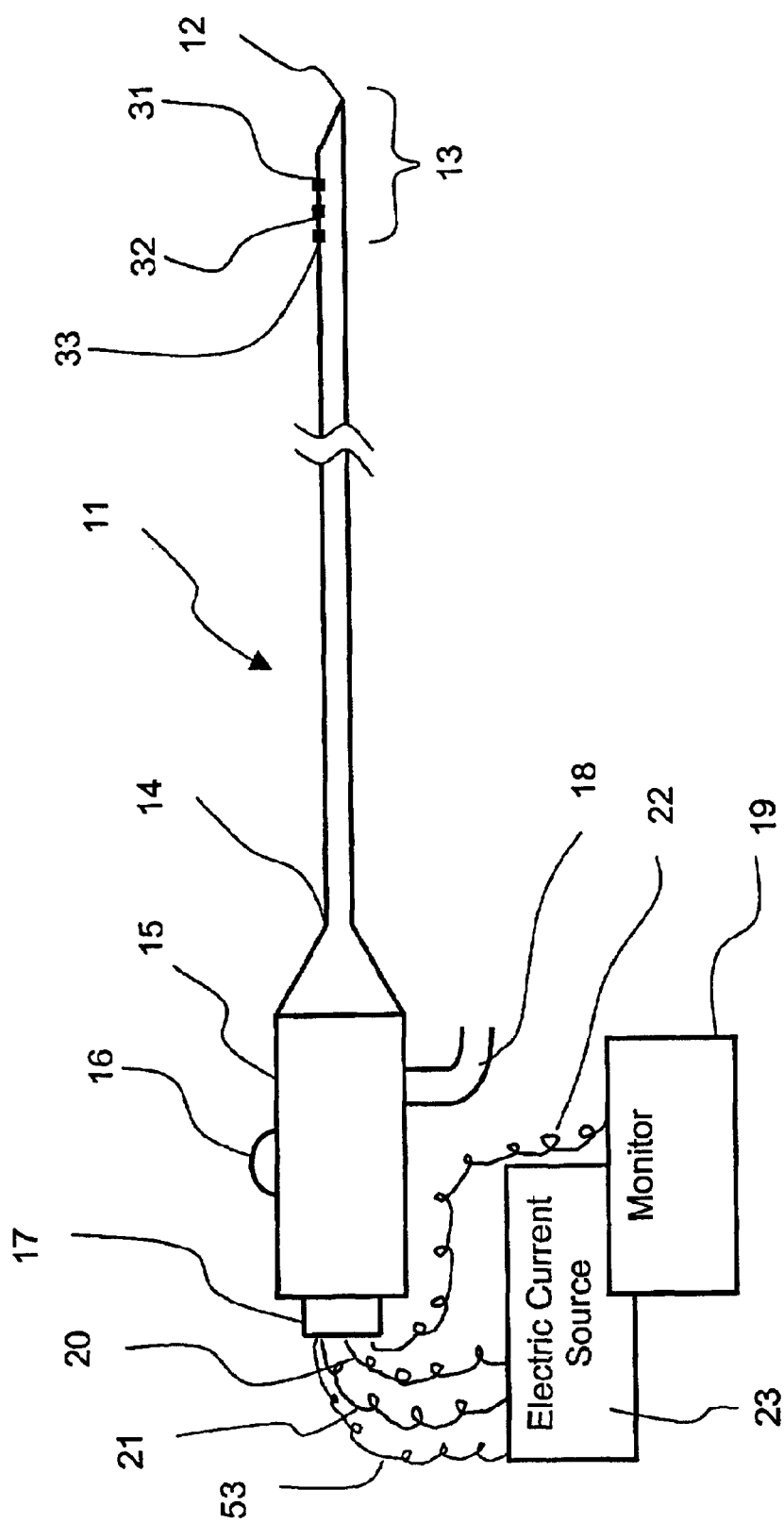
FIG. 1 is an overall view of a medical apparatus constructed in accordance with the principles of the present invention.

It is one object of the present invention to provide an apparatus and a method for enhancedly differentiating in a given area of tissue a tumorous tissue from a normal tissue. The method comprises measuring a plurality of tissue impedance values over a range of tissue temperatures and comparing the measured tissue impedance values with reference tissue impedance values of the normal or non-tumorous tissue adapted for tissue differentiation with high specificity and high sensitivity so as to reduce the numbers of unnecessary biopsy or surgery. The impedance measurement of the present invention may comprise tissue electrical impedance, tissue acoustic impedance, tissue biochemical impedance, and the like.

For background illustration and information, each breast has about 15 to 20 overlapping sections called lobes. Within each lobe are many smaller lobules, which end in dozens of tiny bulbs that can produce milk. The lobes, lobules and bulbs are all linked by thin tubes called ducts, whereby the ducts lead to the nipple in the center of a dark area of skin called the areola. Fat fills the spaces around the lobules and ducts. There are no muscles in the breast.

Each breast also contains blood vessels and lymph vessels. The most common type of breast cancer begins in the lining of the ducts and is called ductal carcinoma. Another type, called lobular carcinoma, arises in the lobules. When breast cancer is found and treated early, the chances for survival are better. A screening mammogram is the best first-step tool available for finding breast cancer early, before symptoms appear. A mammogram is a special kind of x-ray used for checking breast changes in women who have no signs of breast cancer. Although mammograms are the best way to find breast cancer early, they do have some limitations. A mammogram may miss some cancers that are present (false negative) or may find things that turn out not to be cancer (false positive).

Other types of non-invasive breast examinations may include ultrasonography, transspectral impedance scanning or palpation. However, an abnormal area detected by a non-invasive breast screening may cause concern and require further evaluation, typically done by either surgical biopsy or needle biopsy. Although more than a million biopsies are performed each year, only about 15 to 20% of them detect the presence of cancer. This means that the vast majority of biopsies would not need to be performed if an effective screening method could be made available.

Certain electrical properties of tumor cells differ from those of the normal tissues that surround them. Tumor cells demonstrate greater permittivity and conductivity of electrical current. It is reported and generally agreed that cancers have impedance values much lower than those of noncancerous tissue and can be identified by the manner in which they influence the electrical current path. Other tissue properties between normal tissue and tumorous tissue are also parameters for tissue differentiation, particularly over a physiological range of tissue temperatures that are compatible with tissue.

The term "tissue characteristics" herein is intended to mean any or a combination thereof of the following properties: tissue electrical properties (such as electrical impedance, electrical conductance, electrical capacitance, dielectric constants, and the like), biochemical properties (such as oxygen level, pH level, electrolytes concentration, temperature, and the like), structural properties (such as ultrasound signal, acoustic impedance, electromagnetic potential, light transmission, and the like), and physical properties (such as lump, fat tissue density, hardness, appearance, and the like). Most of the tissue characteristics and their first derivative with respect to the tissue temperature are a function of the tissue temperatures.

It is one object of the present invention to differentiate the tissue characteristics by a needle probe operated over a range of tissue temperatures that are compatible with tissue. In one embodiment, the range of controlled tissue temperatures of the present invention is about 20° C. to 45° C. that is suitable and compatible with the body tissue. In another preferred embodiment, the range of controlled tissue temperatures could be from about 20° C. to about 38° C. effected by a cooling mechanism or from 38° C. to about 45° C. effected by a heating mechanism, wherein a healthy person has a normal tissue temperature of about 38° C. A controlled tissue temperatures beyond 20° C. to 45° C. range may also be compatible with the body tissue of some patients.

Curcie and associates reports a study on the role of thermal feedback in electrosurgical tissue heating (Curcie D J et al., *Technology and Health Care*, vol. 3, no. 2, 1995). In the study, a bioheat equation was applied to a resistive model of tissue that showed tissue impedance decreasing with heating in a simulation model. It is further suggested by Curcie et al. from the dynamic interaction study between output power and tissue impedance that the impedance of living tissue generally declines with increasing temperature, a behavior opposite to that of most materials. It is disclosed hereby that the impedance difference between normal tissue and tumorous tissue is enhanced for differentiable tissue diagnosis at a tissue temperature below or above from the normal body temperature, say about 38° C.

It has been found that fatty tissue exhibits significantly different dielectric constant and conductivity than muscle tissue. Since most cancer develops in post-menopausal women (assumed in the age 50 and up group), and since the post-menopausal breast is characterized by a proliferation of adipose (fatty) tissue, it is conceivable to detect cancer in the post-menopausal breast by in situ measurement of the appropriate electrical properties. It is assumed, therefore, that the problem of detecting a tumor in the breast reduces to that of detecting a small region characterized by certain electrical characteristics embedded in a larger region of different electrical characteristics (essentially, those of fat).

A medical probe for in vivo diagnosis and/or therapy has been disclosed in U.S. Pat. No. 6,241,725 to Cosman and No. 6,109,270 to Mah et al., the disclosures of which are incorporated herein by reference. In one particular embodiment, Cosman teaches percutaneously inserting a radiofrequency probe into the tumor and raising the temperature for direct thermal destruction after imaging the tumor by various imaging modalities. As one example, stereotactic methods may be used to locate, calculate, and guide the ablation probes into the region of the tumor, such as real-time CT and MRI imaging. Further, real-time evaluation of the procedures can be carried out using an ultrasonic detector in conjugation and proximity to the radiofrequency electrode.

Referring to FIGS. 1 to 8, what is shown is an embodiment of a medical apparatus or probe having site-specific diagnostic and/or therapeutic capabilities comprising measuring the tissue characteristics, particularly the impedance characteristics, of the target tissue region over a range of tissue temperatures, wherein the tissue temperature is manipulated and controlled by the probe during the diagnosis phase. The apparatus of the present invention may comprise cooling means for achieving the range of tissue temperatures between 20 and 38° C., wherein the cooling means comprises circulating a cooled medium inside said apparatus. In a preferred embodiment, the tissue temperature is manipulated by the Peltier effect mechanism associated with a Peltier effect probe junction mounted onto the medical probe. In one preferred embodiment, the Peltier effect probe junction comprises the impedance-measuring element.

Particularly, the tissue impedance characteristics of the present invention may include the tissue impedance values over the range of temperatures of interest and their first derivatives with respect to temperature. Mathematically, the first derivative of a tissue impedance value over tissue temperature (i.e., "first impedance-temperature derivative") is interpreted as the rate of impedance change with respect to temperature at a tissue temperature of interest. A higher first impedance-temperature derivative indicates more sensitive the change of impedance versus temperature. The tumorous tissue generally has a lower first impedance-temperature derivative than that of a normal tissue. In other words, the tumorous tissue impedance is generally less sensitive to tissue temperature change than that normal tissue impedance.

FIG. 1 shows an overall view of a medical apparatus constructed in accordance with the principles of the present invention. The medical apparatus of the present invention may comprise a catheter, a probe, a cannula, an endoscopic instrument, a lapascopic instrument or the like that is suitable for the intended applications in differentiating and/or treating tumorous tissue. By "tumorous tissue" is meant herein for any abnormal tissue including tumor, cancerous tissue, arrhythmia, pulmonary vein, benign prostate hyperplasia, breast tumor, breast cancer, inflammation, atherosclerosis, abnormal brain tissue, vulnerable plaque, or the like inside the body of a patient. It is one object of the present invention to provide an apparatus of differentiating in a given area of tissue an abnormal or tumorous tissue from a normal tissue, the apparatus and method comprising measuring a plurality of tissue impedance readings over a range of tissue temperatures and comparing the measured tissue impedance readings with reference tissue impedance of the acceptable representative normal tissue adapted for qualitative and/or quantitative tissue differentiation. The tissue impedance reading of the present invention may be obtained at any temperature between, say 20° C. and 45° C. range.

In one embodiment, the medical probe 11 comprises a flexible or rigid probe body having a distal end 12, a proximal end 14, at least a lumen therebetween, and a distal section 13. A handpiece 15 is attached to the proximal end 14 of the probe body. The probe may be provided at its proximal end a connector 17 to an external electric current source 23 having a plurality of insulated conducting wire sets 20, 21 for providing current to a metallic element assembly (heating or cooling) comprising a plurality of impedance measuring elements 31, 32, 33 at the probe distal section 13. The impedance measuring transmission arrangement 22 is provided from the connector 17 to the monitor setup 19. The electric current source 23 may be a high frequency current source or other energy source, for example radiofrequency energy, ultrasound energy, infrared energy, laser energy, microwave energy, Peltier effect, cryogenic energy, or the like. The impedance measuring transmission arrangement 22 also functions as a temperature monitoring transmission.

The distal section 13 and the distal end 12 of the probe 11 may be configured for easy insertion into a tissue of a patient with a small incision. The sharpness of the distal end 12 is suitable for insertion and the probe body is generally smooth with optional hydrophilic or anti-adhesive surface coating. The probe can be a cylindrical, oval or other suitable configuration with optional side or end openings. The outer diameter of the probe is preferable less than 5 mm, more preferably 2 mm or smaller. The probe can be several inches or longer suitable for intended applications. To enhance tissue contact with the impedance measuring elements, the section of the probe containing the impedance measuring elements 31, 32, and/or 33 may be constructed bulged outwardly. The arrangement of the impedance measuring elements may be spaced apart axially, circumferentially, combination thereof, or mounted on separate micro-needles that are secured at the distal end 12 of the probe 11.

The probe handpiece 15 may also comprise at least a switch control arrangement 16 provided to control the electrical current, the current flow direction, impedance measurement, temperature sensing, and other operating conditions. In a preferred embodiment, the electrical conductor arrangement 53 is to provide an electrical current to the impedance-measuring element 31, 32, 33 or equivalent for a monopolar-mode or bipolar-mode impedance measurement. In operation, when the impedance measuring elements contact a tissue, the first tissue impedance between the elements 31 and 32 can be measured. Similarly, the second tissue impedance between the elements 32 and 33 can be measured. In this illustrated case, the first tissue impedance might indicate an abnormal tissue while the second tissue impedance might indicate a normal tissue or vice versa. The probe of the present invention may further comprise at least three spaced apart micro-electrode elements for measuring tissue impedance, the measured tissue impedance from a first and a second of the at least three micro-electrode elements being compared to the measured tissue impedance from the second and a third of the at least three micro-electrode elements for tissue differentiation.

The impedance measuring elements 31, 32, 33 may be made of any suitable material that is most efficient to sense the impedance signals. The suitable material may include conductive metal such as gold, silver, platinum, stainless steel, Nitinol, metal alloy, or conductive plastics. The spacing between any two measuring elements is pre-determined and is generally about 0.1 mm to 2 mm in a bi-polar measuring mode.

Because cancers have impedance values substantially lower than benign or normal tissue, they can be identified by their effects in altering the electrical current path. Typically a low voltage of about 1.0 volt is applied directly to the patient through the measuring elements of a medical probe. The frequencies can vary or pre-programmed between 50 Hz to about 50 kHz or higher. There are three basic methods for measurement of electric impedance: bridge, voltage and current method. The last one can be applied in two variations on electrodes number: bipolar and tetrapolar. In impedance spectrometry a generator with changeable frequency from few Hz to kHz or MHz is used. The tetrapolar current method is the best for measuring of tissue impedance because of its independence from electrode-skin impedance variability and homogeneous distribution of current density. To mitigate the influence of artifacts on measuring results, the impedance spectrometry may have a special arrangement with fast result analysis for detection and automatic elimination of artifacts by repetition of measurement. In practice, a small constant current, typically 800 μAmp at a fixed frequency, usually 50 kHz, is passed between electrodes 31, 32 through the tissue and the voltage drop between electrodes provides a measure of impedance. The principles of impedance measurement and bi-polar impedance measuring methods are well known to those who are skilled in the art and do not constitute a part of the present invention.

The measured impedance data is fed to an external monitor 19, which may be connected to the electric current source 23 for feedback or closed-loop current control. For "monitor" is meant herein an instrument that can store, analyze, compare, and report data, wherein the monitor has a computer software comparing real-time measurements to a set of archived parameters that indicate the presence or absence of cancer. The computer software also has the processing capability by comparing the measured tissue impedance and first impedance-temperature derivative over at least a portion of the range of tissue temperatures with reference tissue impedance and first impedance-temperature derivative of the normal tissue adapted for tissue differentiation, wherein said reference tissue impedance is measured over the range of tissue temperatures. The results as displayed on the monitor instantly should help doctors make the right diagnosis early and develop a treatment plan for the patient. The probe may further comprise an optional attachment 18 configured and adapted for delivering therapeutic means for treating the tumorous tissue at about the target area of tissue, wherein the target area of tissue may comprise breast tissue, prostate tissue, brain tissue, or the like as defined in the term "tumorous tissue" of the present invention. Further, the therapeutic means of the present invention may be selected from a group consisting of drug, chemotherapy, radiation, and combination thereof, which are all well known means for cancer treatment.

Tumor is an abnormal mass of tissue that results from excessive cell division. Tumor performs no useful body function and could be either benign or malignant. Cancer is a disease in which abnormal cells divide without control; cancer cells can invade nearby tissues and can spread through the bloodstream or lymphatic system to other parts of the body. One characteristic for cancer is its ample supply of blood through abnormally large numbers of capillaries. Therefore, it is conceivable that at an elevated tissue temperature, the lowering of the impedance for normal tissue may be faster than that of tumorous tissue due to the warm-blood effect. In another disclosure, it is also conceivable that the increase of the impedance for normal tissue at a lowered tissue temperature may be faster than that of tumorous tissue due to similar warm-blood effect.

Figure 2:
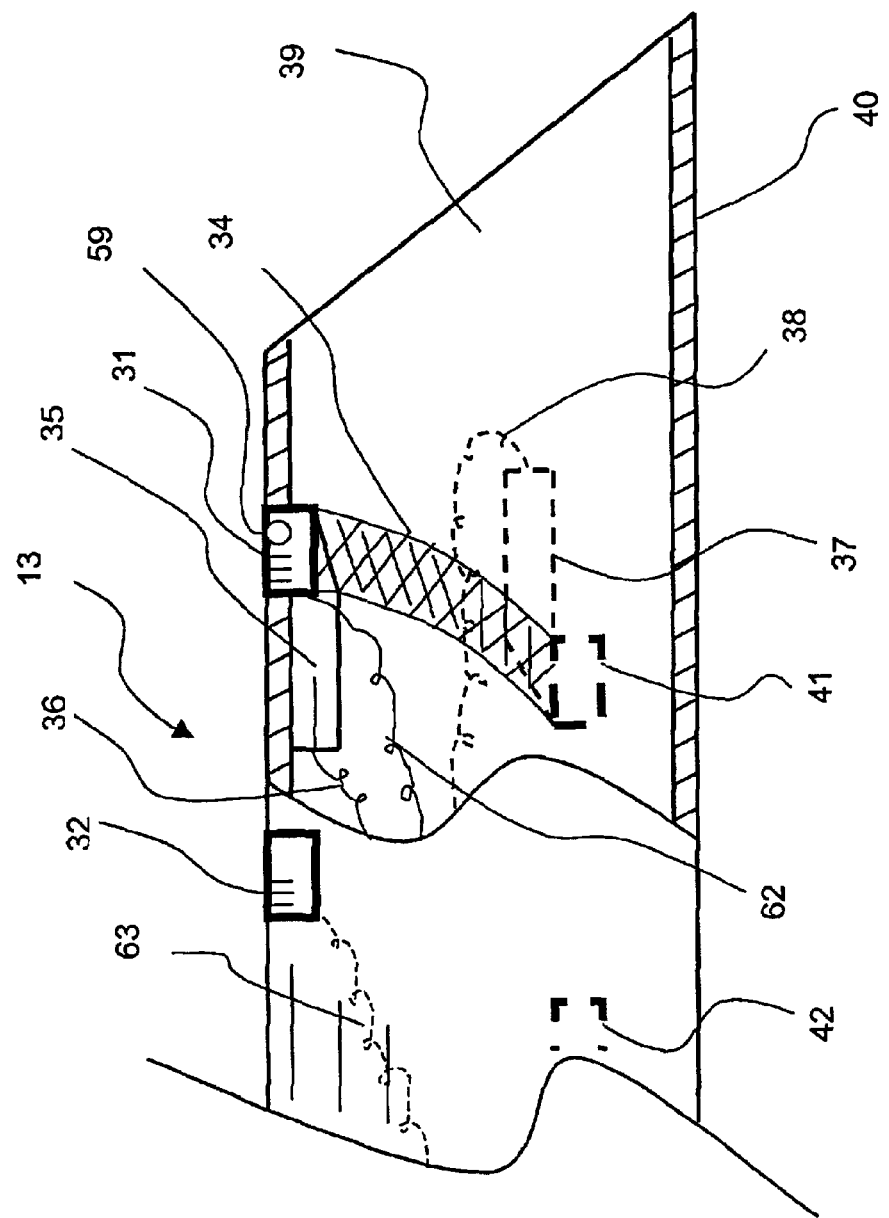
FIG. 2 is a cross-sectional view of the tip section assembly of the medical apparatus, showing impedance measuring elements and two elements of different electromotive potential conductively connected at a probe junction.

FIG. 2 shows a cross-sectional view of the tip section assembly 13 of the medical probe 11, showing impedance measuring elements 31, 32 and elements 35, 37 of different electromotive potential conductively connected at a probe junction 34. The "probe junction" of the present invention is intended to mean a junction with a somewhat curved configuration to provide cryogenic energy or thermal energy around or surround the metallic element assembly or equivalent adapted for adjusting the temperature of the impedance measuring elements 31, 32 over a range of temperatures.

In an alternate embodiment the probe junction of the present invention may serve as the tissue measuring element or the therapeutic energy-treating element. Further, the probe junction may be selected from a group consisting of circular, semi-circular, ring, rounded, oval, random curved shape or other suitable configuration. In an alternate embodiment, an opening 39 at the distal end 12 of the medical probe 11 is configured and adapted for delivering therapeutic means for treating the tumorous tissue in situ. In a further alternate embodiment, the probe junction of the Peltier effect of the present invention may be installed on the medical probe apart from the impedance measuring elements 31, 32, and/or 33. The probe may further comprise indirect means for providing cryogenic energy or thermal energy from the probe junction to the metallic element assembly or equivalent adapted for adjusting the temperature of the impedance measuring elements 31, 32, 33 over a range of temperatures.

Figure 4:
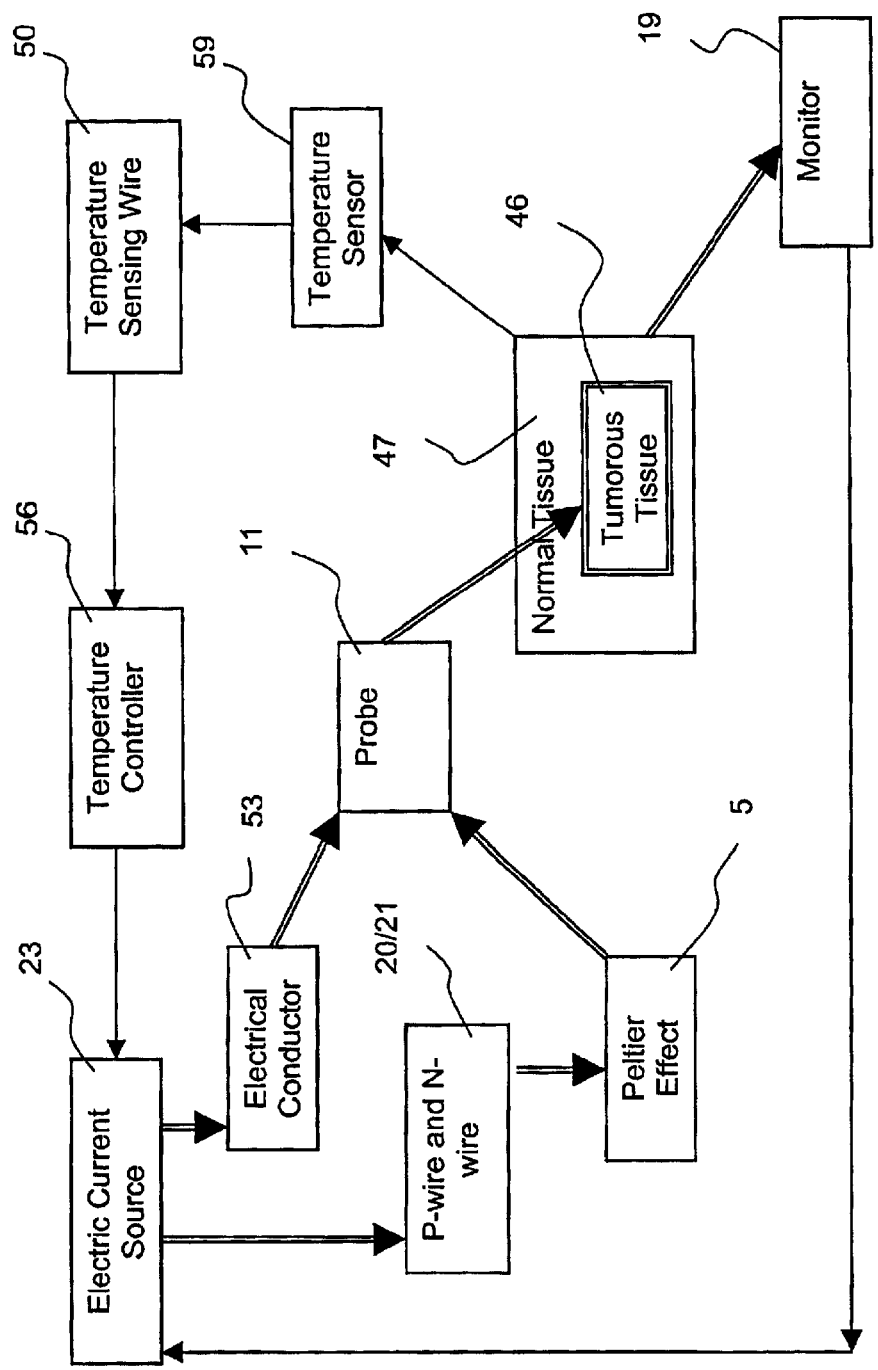
FIG. 4 is a schematic illustration of the principles of the medical probe for tumor diagnosis.

According to the principles of the present invention as illustrated in FIG. 4, the medical probe 11 may optionally comprise a temperature sensor 59 secured at about the tissue measuring elements 31, 32, or 33 for monitoring the tissue temperature, wherein the measured temperature is relayed through a temperature sensing wire 50 to a monitor or to a temperature controller 56 for controlling the thermal/cryogenic energy supply, when needed.

Figure 3:
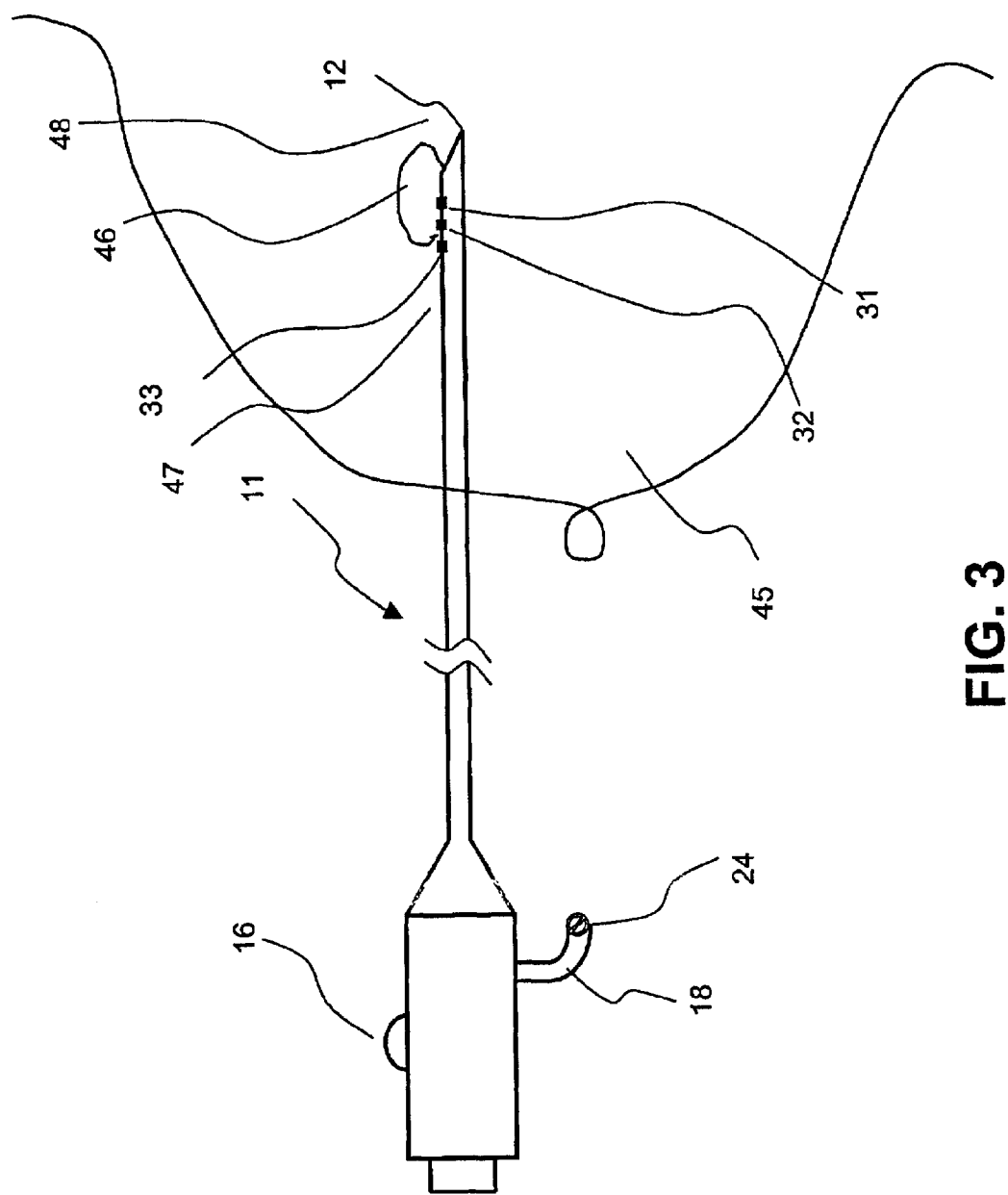
FIG. 3 is a simulated view of the medical probe inserted into a breast for tissue differentiation.
Figure 6:
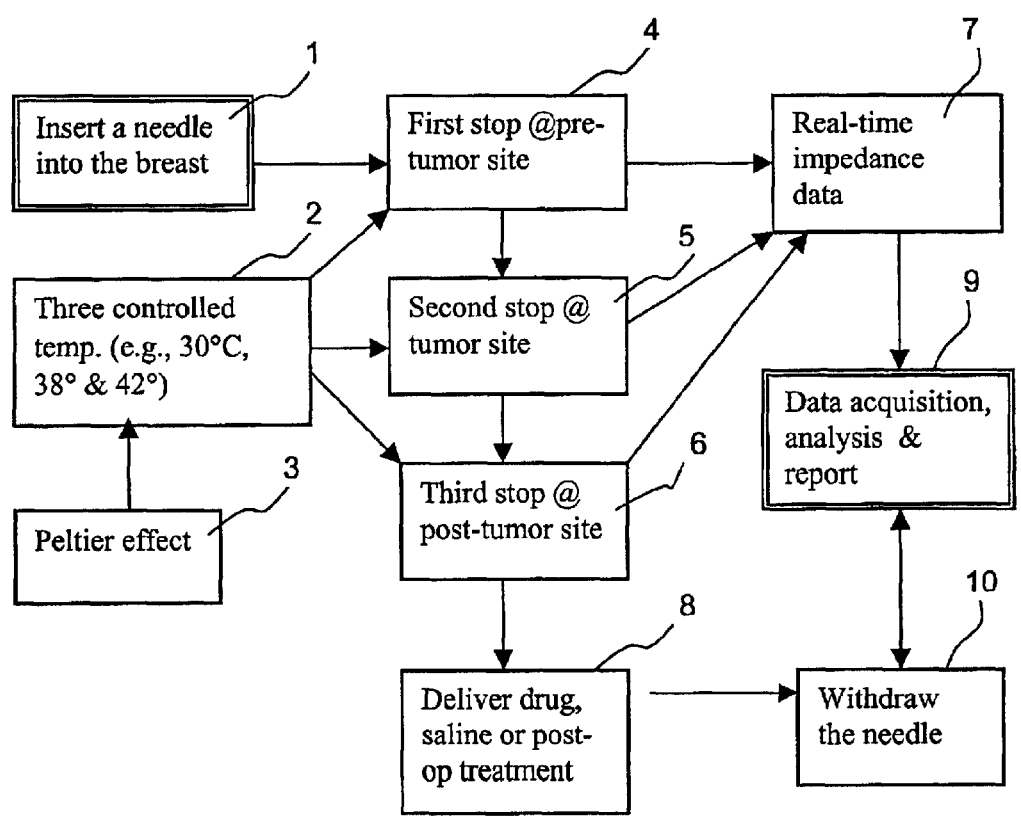
FIG. 6 is a schematic diagram illustrating the methods for operating a medical probe according to the principles of the present invention.

FIG. 3 shows a simulated view of the medical probe inserted into a breast for tissue differentiation while FIG. 6 shows a schematic diagram illustrating the methods for operating a medical probe according to the principles of the present invention. For illustration purposes by referring to FIGS. 3 and 6 simultaneously, a medical probe 11 is inserted (step 1) into the breast 45 of a patient approaching the target tissue zone 46. The probe passes and briefly stops (step 4) at a pre-tumor site 47 for measuring the impedance characteristics (step 7) over a range of tissue temperatures. The tissue temperature is manipulated (step 2) by the Peltier effect mechanism (step 3) built-in with the probe; for example a tissue temperature of 30° C., a normal body temperature of 38° C., a tissue temperature of 42° C. or others. The mode of operating heating and cooling of the present invention according to the Peltier effect may be a simultaneous, an alternate, a sequential, other pre-programmed mode, or combination thereof. At each site, the tissue characteristics, such as the impedance, the temperature, the first impedance-temperature derivative and the like are measured, processed and archived.

As the medical probe 11 advances further (step 5) into the tumorous tissue zone 46, the impedance tissue readings (step 7) at certain tissue temperatures (step 2) are taken either continuously or time-discretely. To obtain further reference readings from normal tissue, the medical probe 11 may stop (step 6) briefly at a post-tumor site 48. All data are fed (step 9) to the monitor 19 for data acquisition, analysis, processing and report. In an alternate embodiment, the medical probe 11 may be configured for delivering drug, saline or other post-treatment therapy (step 8). The probe comprises delivering therapeutic means for treating the tumorous tissue at about the target tumorous tissue, wherein the therapeutic means is selected from a group consisting of drug, chemotherapy, radiation, and combination thereof. The therapeutic means may further comprise a step of providing thermal energy, cryogenic energy or combination thereof, to treat the tumorous tissue. The activating mechanism 24 (FIG. 3) for triggering the therapeutic means is mounted at about the attachment 18 of the probe 11.

Blewett et al. in U.S. Pat. No. 6,106,521 discloses an apparatus with a needle-like probe for thermal treatment of tissue. Behl in U.S. Pat. No. 6,212,433 discloses a system for treating a target tissue beneath a tissue surface by deploying a needle-like electrode array. Durgin, Jr. et al. in U.S. Pat. No. 5,522,815 discloses an integrated catheter with a needle for diverse in situ tissue therapy. Mulier et al. in U.S. Pat. No. 6,238,393 discloses an apparatus for creating a bi-polar virtual electrode through a needle-like inner electrode. The contents of all the above-cited patents are incorporated herein by reference. A needle or needle-like electrode for penetrating into a tissue is well known to one ordinary artisan skilled in the art of electrode ablation. None of the above-referred prior art teaches an apparatus and methods for sensing and comparing tissue impedance or first impedance-temperature derivative over a range of tissue temperatures with reference tissue impedance or corresponding first impedance-temperature derivative of the normal tissue adapted for tissue differentiation, wherein the reference tissue impedance values are measured over the same range of tissue temperatures.

As described in U.S. Pat. No. 4,860,744, U.S. Pat. No. 5,529,067 and generally shown in FIG. 5 of the present invention, general principles of the Peltier effect are illustrated below as a supporting example. The therapeutic element 81 utilizes one pair of P (positive) and N (negative) thermoelectric elements or legs. The materials of the thermoelectric therapeutic element 81 may be configured in a variety of different ways such as bar or wire forms design. The P leg 82 and N leg 83 are electrically separated along their lengths, but are conductively joined at one end. The contact junctions 86, 87 represent one of junctions. With reference to U.S. Pat. No. 4,860,744, a molybdenum silicide plate to join the two legs at the contact junctions 86, 87 may be optionally used. The molybdenum silicide plate, as one example, that connects the legs at the contact junction 86, 87 is referred to as a cool junction "shoe" 80 (can be a hot junction shoe if the current is reversed). The P and N legs are separately connected at a second end to connector wires 84, 85. The ends of the thermoelectric elements are referred as junctions. The other set of junctions are the reference junctions 89, 90. The manner in which P and N legs are formed and the Peltier effects is known to those skilled in the art and forms no part of the present invention.

Figure 5:
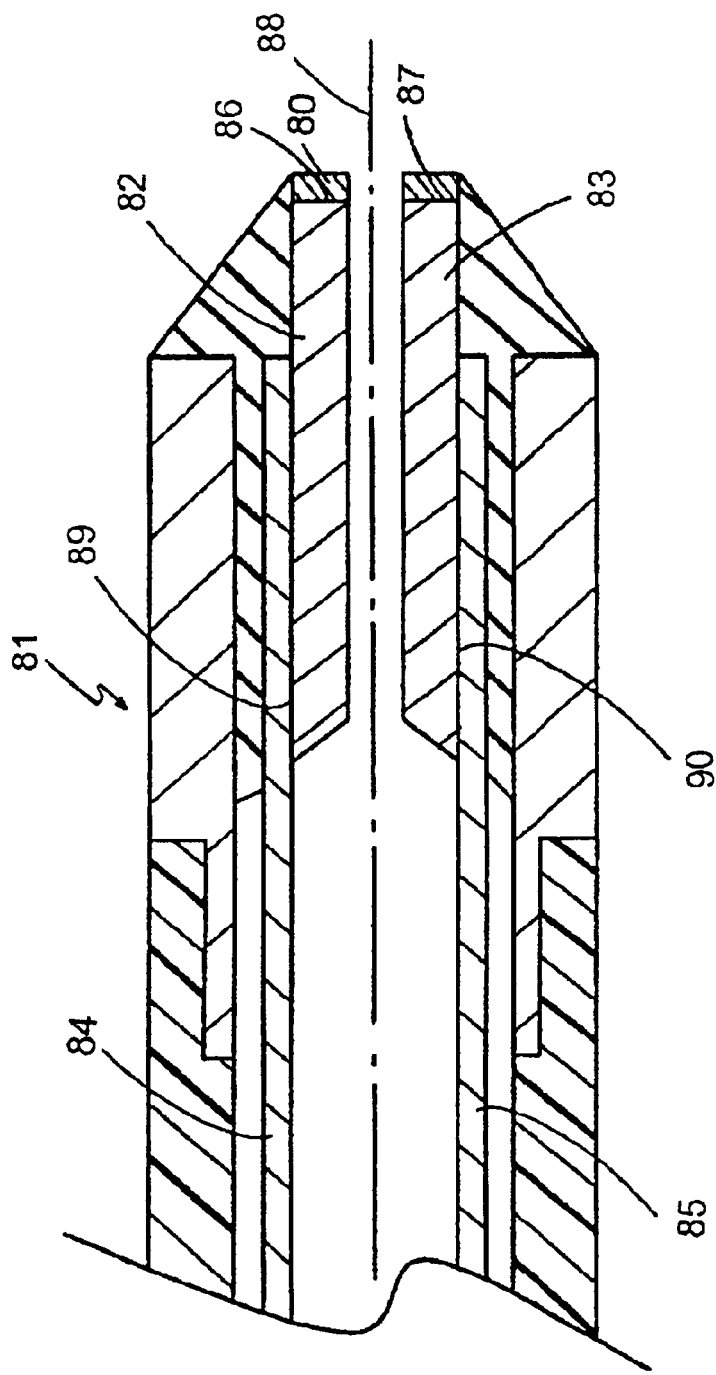
FIG. 5 is a longitudinal cross-sectional view of the distal end portion of a representative apparatus utilizing the Peltier effect as an example.

Referring to FIG. 5, thermoelectric cooling of the contact junctions 86, 87 occurs when an electrical current is passed through the legs in the N to P direction, which is controlled by the power switch control 16 at the handpiece 15. The reference junctions 89, 90 experience heating when this electrical current is passed through the legs. Additional Joulean heating occurs in the legs 82, 83 because of the internal electrical resistance of the legs. This Joulean heating diminishes the cooling of the cold junction shoe 80. There is a need to disperse the heat generated at the legs and at the reference junctions 89, 90. The reference junction is illustratively represented with elements 41, 42 in FIG. 2.

As shown in FIG. 2, the electromotive elements 35 and 37 for the probe junction 34 are configured and arranged so that the reference junctions 41, or 42 are adjacent a surface of the probe body 40. By such an arrangement, the heat generated at the reference junctions does not interfere with the tissue temperature of interest. Therefore, the probe junction 31 or 32 can maintain its coolness (or heat) effective for measuring the tissue impedance over a range of tissue temperatures that are physiologically compatible to tissue. In a certain embodiment, the probe junction 31 may preferably be configured permeably porous for fluid or small particles, such as electrolytes, to flow through. The flow-through fluid may stabilize the impedance readings with little noise. In another embodiment, the probe junction is impermeable to any fluid or particles.

The acoustic impedance is a property of tissues that depends on the speed of sound and the tissue's density. Acoustic impedance is important because it is involved with reflection and production of echoes from tissues. The term "acoustic impedance" as used herein is not ultrasound attenuation. The acoustic impedance is found by multiplying a tissue's speed of sound times its density. In general, impedances of soft tissues differ from one another by only a small amount. As an ultrasound pulse propagates through tissue, any interface formed by two tissues that have different acoustic impedances will cause some of the sound energy to be reflected. The difference in acoustic impedances between the normal tissue and the tumorous tissue is crucial in determining the amount of sound reflected versus the amount transmitted at the interface, wherein the difference in acoustic impedances is a tissue characteristic that is used for tissue differentiation of the present invention. It is further disclosed that the difference in acoustic impedances between the normal and the tumorous tissues is amplified or diminished over a range of tissue temperatures. The difference in acoustic impedances over a range of tissue temperatures is used for tissue differentiation of the present invention.

The term "biochemical tissue impedance" is meant to indicate herein the impedance (also known as resistance to measuring techniques in this embodiment) relating to the biochemical properties of tissue for tissue differentiation between normal tissue and tumorous tissue. The biochemical tissue impedance may comprise oxygen level, pH level, temperature due to inflammation, and the like. A probe or microprobe element for measuring partial pressure of oxygen can be mounted at the probe tip section 13 that can aid in detection of hypoxia, an indication of tumor malignancy. An ion-selective micro-electrode element for measuring the tissue pH and a thermometer element for measuring the tissue temperature can also be mounted at the probe tip section 13 adapted for the intended diagnosis of biochemical tissue impedance over a range of tissue temperatures that is manipulated and controlled through the medical probe of the present invention.

A miniature probe that incorporates an ultrasonic sensor could facilitate early diagnosis of cancer or tumor. When evaluating a potentially cancerous tumor, a pathologist will look for certain features in cell structure and growth pattern through a biopsy. Nevertheless, by examining the size and shape of the cells in vivo and how they interact with surrounding tissue, a determination can be made whether the tumor is malignant or benign. A tiny ultrasound transducer can be fabricated on an apparatus, such as a needle, operated in vivo at high frequency up to 300 MHz. It is known that operating at a frequency of 100 MHz to 300 MHz, the ultrasound apparatus would have an image resolution comparable to what a pathologist sees when examining tissue under a microscope. The pathologist could thus use the minimally invasive procedures to achieve the same goal as a surgical biopsy.

The ultrasound transducer has an inner layer and an outer layer for transmitting the ultrasonic signals and receiving the returned signals. Typically the inner layer and the outer layer are made of conductive material with a ceramic barrier in-between. The outer layer may be configured and adapted as a tissue impedance measuring element. For example, the outer layer serves as one of the bi-polar electrodes in a tissue impedance measurement apparatus. Such an outer layer may also serve as the junction or measuring point for a thermocouple measurement setup.

Figure 7:
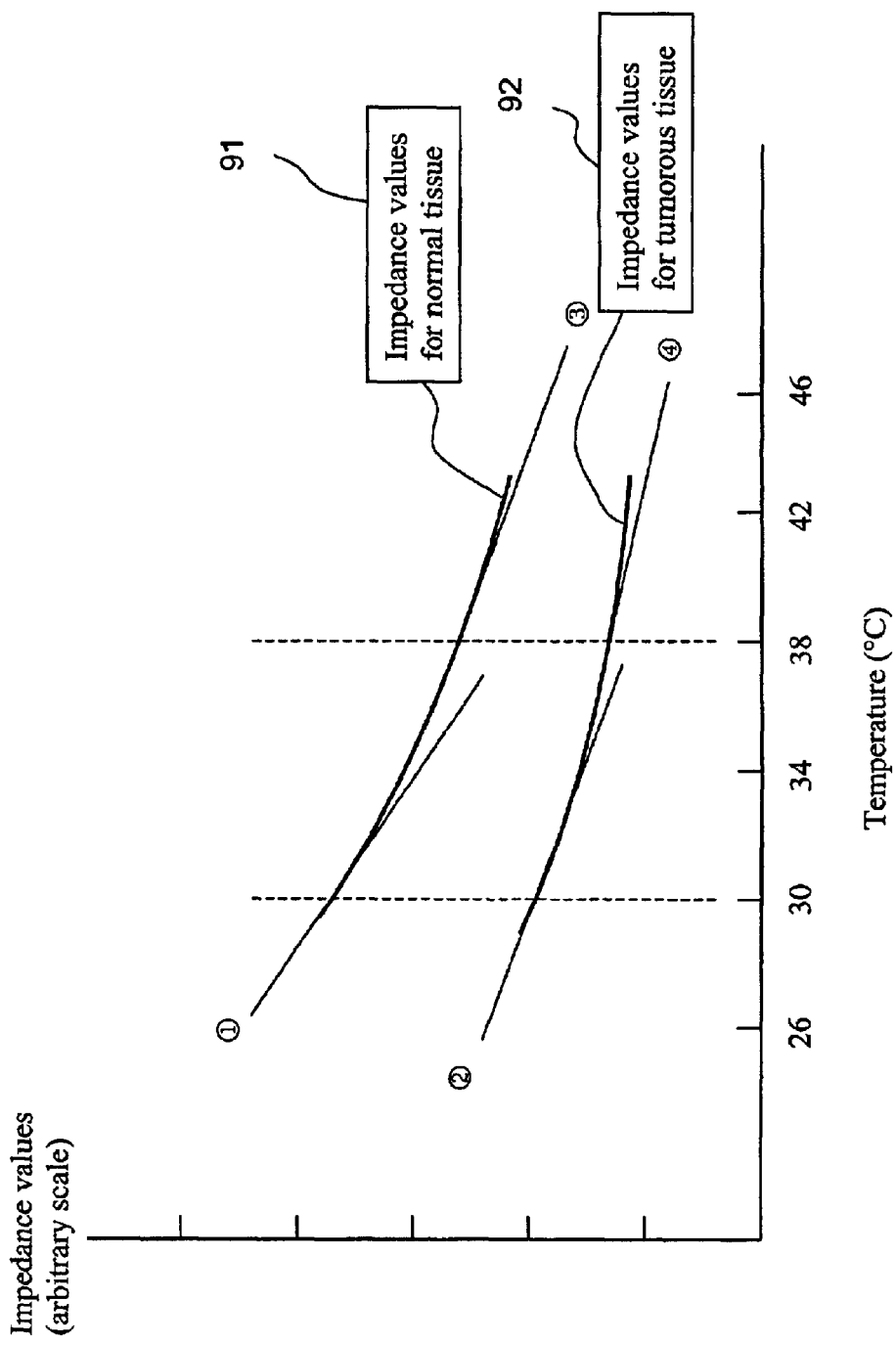
FIG. 7 is a first simulated impedance versus tissue temperature trend with a generally concave curve.

The tissue impedance values over a range of temperature may be affected by the tissue structure, tissue property, tissue density, extracellular medium, intracellular composition, tissue pathological characteristics, and other factors. The impedance value as a function of tissue temperature is therefore conceived to show like a generally concave trend, convex trend, or a combination thereof. For illustration purposes, FIG. 7 shows a simulated impedance versus tissue temperature trend with a generally concave curve. The impedance values for normal tissue 91 and the impedance values for tumorous tissue 92 at an arbitrary scale are shown over a range of temperatures of interest. The literature data has shown that the impedance values for tumorous tissue are generally lower than those for normal tissue. The slope of the impedance values with respect to the temperature is called "first temperature-impedance derivative" and represents the rate of change of the tissue impedance values at any specific tissue temperature. Therefore, the first temperature-impedance derivatives for normal tissue and tumorous tissue of FIG. 7 at 30° C. are designated as slopes ① and ②, respectively. Similarly for example, the first temperature-impedance derivatives for normal tissue and tumorous tissue of FIG. 7 at 38° C. are designated as slopes ③ and ④, respectively. The slope values between the pair ① and ② or between the pair ③ and ④ could be statistically significant in tissue differentiation. Once the slopes are determined by the medical apparatus of the present invention by the processing means for analyzing tissue impedance data over the range of tissue temperatures, the first impedance-temperature derivative at a tissue temperature of interest with reference first impedance-temperature derivative of the normal tissue at at least one tissue temperature of interest could be adapted for tissue differentiation.

Figure 8:
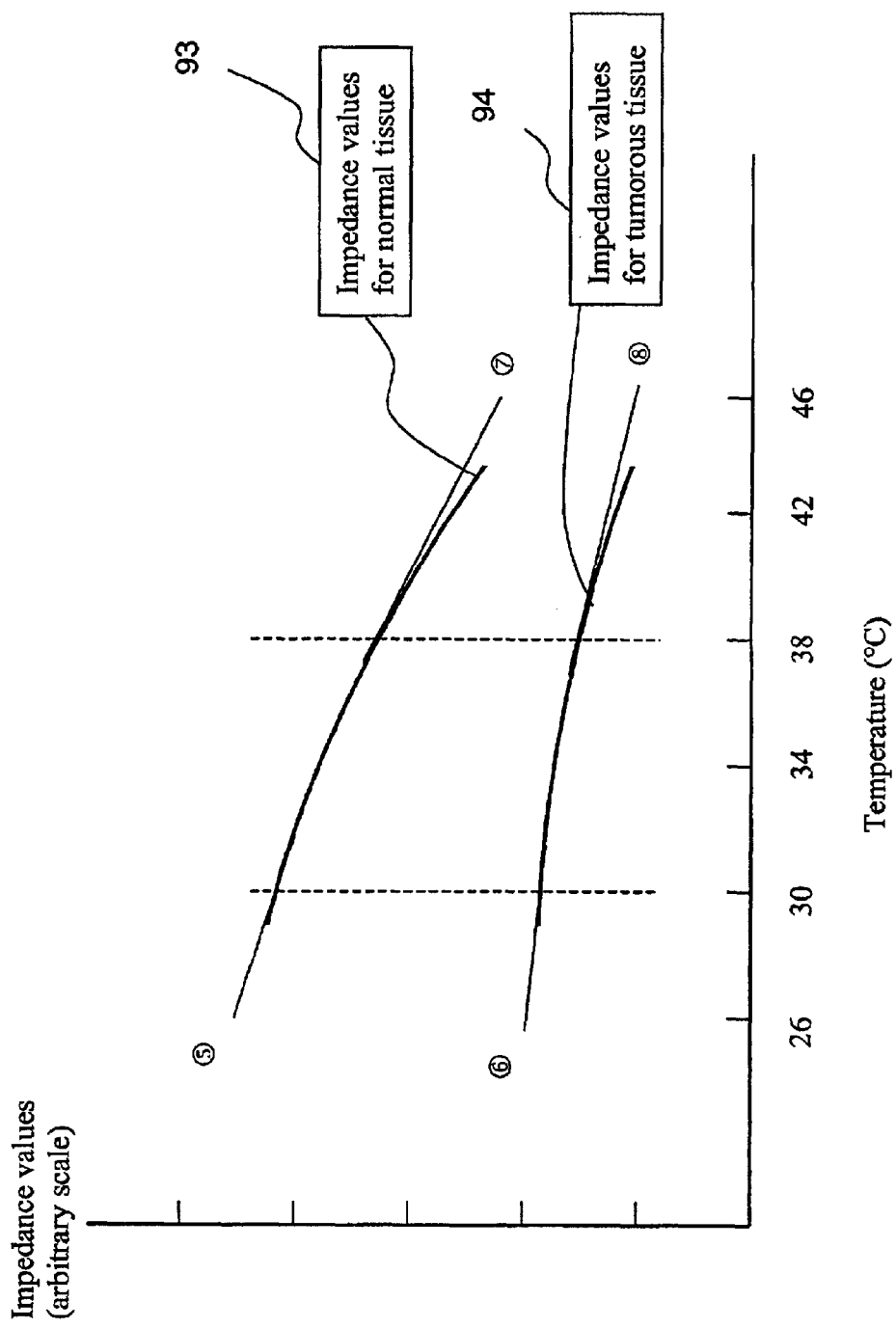
FIG. 8 is another simulated impedance versus tissue temperature trend with a generally convex curve.

FIG. 8 shows another simulated impedance versus tissue temperature trend with a generally convex curve, as an illustration. The impedance values for normal tissue 93 and the impedance values for tumorous tissue 94 at an arbitrary scale are shown over a range of temperatures of interest. The first temperature-impedance derivatives for normal tissue and tumorous tissue of FIG. 8 at 30° C. are designated as slopes ⑤ and ⑥, respectively. Similarly for example, the first temperature-impedance derivatives for normal tissue and tumorous tissue of FIG. 8 at 38° C. are designated as slopes ⑦ and ⑧, respectively. The slope values between the pair ⑤ and ⑥ or between the pair ⑦ and ⑧ could be statistically significant in tissue differentiation. Once the slopes are determined by the medical apparatus of the present invention by the processing means for analyzing tissue impedance data over the range of tissue temperatures, the first impedance-temperature derivative at a tissue temperature of interest with reference first impedance-temperature derivative of the normal tissue at at least one tissue temperature of interest could be adapted for tissue differentiation.

It is therefore discloses that an apparatus for differentiating in a given area of tissue a tumorous tissue from a normal tissue comprises: (a) electrode means for continuous or time-discrete measurement of tissue impedance over a range of tissue temperatures; (b) instrument means for effecting and monitoring said tissue temperatures; (c) processing means for analyzing tissue impedance data over the range of tissue temperatures to obtain a first impedance-temperature derivative of the tissue impedance versus tissue temperatures; and (d) comparing said first impedance-temperature derivative at a tissue temperature of interest with reference first impedance-temperature derivative of the normal tissue at said tissue temperature of interest adapted for tissue differentiation.

From the foregoing description, it should now be appreciated that a medical apparatus and methods comprising incorporating a method of differentiating in a given area of tissue a tumorous tissue from a normal tissue, the method comprising measuring a plurality of tissue impedance characteristics over a range of tissue temperatures and comparing the measured tissue impedance characteristics with reference tissue impedance characteristics of the normal tissue adapted for enhanced tissue differentiation has been disclosed. While the invention has been described with reference to a specific embodiment, the description is illustrative of the invention and is not to be construed as limiting the invention. Various modifications and applications may occur to those who are skilled in the art, without departing from the true spirit and scope of the provisional application.

What is claimed is:

1. An apparatus for differentiating in a given area of tissue a tumorous tissue from a normal tissue, comprising:

electrode means for continuous or time-discrete measurement of tissue impedance over a range of tissue temperatures;

instrument means for effecting and monitoring said tissue temperatures; and means for comparing said measured tissue impedance over at least a portion of the range of tissue temperatures with reference tissue impedance of the normal tissue adapted for tissue differentiation, wherein said reference tissue impedance is measured over said range of tissue temperatures, wherein said range of tissue temperatures is between 20° C. and about 38° C.

2. The apparatus of claim 1, wherein said instrument means further comprises a thermoelectric device using Peltier effect for achieving said range of tissue temperatures.

3. The apparatus of claim 2, wherein said thermoelectric device comprises elements of different electromotive potential conductively connected at a probe junction adjacent said electrode means; and current means for passing an electrical current through said elements to reduce or raise temperature of said probe junction in accordance with the Peltier effect.

4. The apparatus of claim 1, wherein the instrument means for monitoring said tissue temperatures comprises a temperature sensor at about said electrode means of the apparatus.

5. The apparatus of claim 1, wherein the instrument means for effecting said tissue temperatures comprises radiofrequency heating and circulating a cooled medium inside said apparatus.

6. The apparatus of claim 1 further comprising cooling means for achieving said range of tissue temperatures between 20 and 38° C., wherein the cooling means comprises circulating a cooled medium inside said apparatus.

7. An apparatus for differentiating in a given area of tissue a tumorous tissue from a normal tissue, comprising:
- electrode means for continuous or time-discrete measurement of tissue impedance over a range of tissue temperatures;
- instrument means for effecting and monitoring said tissue temperatures;
- processing means for analyzing tissue impedance data over the range of tissue temperatures to obtain a first impedance-temperature derivative of the tissue impedance versus tissue temperatures; and
- means for comparing said first impedance-temperature derivative at a tissue temperature of interest with reference first impedance-temperature derivative of the normal tissue at said tissue temperature of interest adapted for tissue differentiation.

8. The apparatus of claim 7, wherein said range of tissue temperatures is between 20° C. and 45° C.

9. The apparatus of claim 7, wherein said instrument means further comprises a thermoelectric device using Peltier effect for achieving said range of tissue temperatures, said thermoelectric device comprising elements of different electromotive potential conductively connected at a probe junction adjacent said electrode means and current means for passing an electrical current through said elements to reduce or raise temperature of said probe junction in accordance with the Peltier effect.

10. The apparatus of claim 7, wherein the instrument means for monitoring said tissue temperatures comprises a temperature sensor at about said electrode means of the apparatus.

11. The apparatus of claim 7, wherein the instrument means for effecting said tissue temperatures comprises radiofrequency heating and circulating a cooled medium inside said apparatus.

12. The apparatus of claim 7 further comprising cooling means for achieving said range of tissue temperatures between 20 and 45° C., wherein the cooling means comprises circulating a cooled medium inside said apparatus.

13. The apparatus of claim 7 further comprising treating means for delivering therapeutic drugs for treating the tumorous tissue at about said given area of tissue.

14. The apparatus of claim 7 further comprising treating means for delivering non-drug therapy for treating the tumorous tissue at about said given area of tissue, wherein said non-drug therapy is selected from a group consisting of chemotherapy, radiation, thermal energy, cryogenic energy, and combination thereof.

15. The apparatus of claim 7 further comprises an ultrasonic sensor with an ultrasound transducer having an outer layer, wherein the electrode means comprises said outer layer of the ultrasound transducer of said ultrasonic sensor.

16. The apparatus of claim 15, wherein the ultrasound transducer comprises an operating frequency up to 300 MHz.

17. A method of differentiating in a given area of tissue a tumorous tissue from a normal tissue, comprising:
a) advancing an apparatus to said given area, wherein said apparatus comprises electrode means for continuous or time-discrete measurement of tissue impedance over a range of tissue temperatures and comprises instrument means for effecting and monitoring said tissue temperatures;
b) acquiring tissue impedance data over the range of tissue temperatures to obtain a first impedance-temperature derivative of the tissue impedance versus tissue temperatures; and
c) comparing said first impedance-temperature derivative at a tissue temperature of interest with reference first impedance-temperature derivative of the normal tissue at said tissue temperature of interest adapted for tissue differentiation.

18. The method of claim 17, wherein said given area of tissue is selected from a group consisting of breast tissue, prostate tissue, and brain tissue.

19. The method of claim 17, further comprising a step for treating the tumorous tissue at about said given area of tissue by delivering therapeutic drugs.

20. The method of claim 17, further comprising a step for treating the tumorous tissue at about said given area of tissue by applying non-drug therapy, wherein said non-drug therapy is selected from a group consisting of chemotherapy, radiation, thermal energy, cryogenic energy, and combination thereof.

* * * * *